United States Patent [19]

Revici

[11] Patent Number: 4,701,442

[45] Date of Patent: Oct. 20, 1987

[54] TREATMENT OF SYMPTOMS OF NEOPLASTIC DISEASES WITH NUCLEOPROTEINS

[75] Inventor: Emanuel Revici, New York, N.Y.

[73] Assignee: Elena Avram, New York, N.Y.

[21] Appl. No.: 744,341

[22] Filed: Jun. 13, 1985

[51] Int. Cl.$^4$ ............................................. C07K 15/18
[52] U.S. Cl. ...................... 514/21; 530/358; 530/370; 530/371; 530/407; 530/820; 530/821; 530/823; 530/825; 530/844; 530/846; 530/852; 530/837; 530/838
[58] Field of Search ............... 530/358, 407, 370, 371, 530/820, 821, 823, 825, 844, 846, 852, 837, 838; 514/21

[56] References Cited

U.S. PATENT DOCUMENTS

| 637,353 | 11/1899 | Schwickerath | 530/358 |
| 2,115,751 | 4/1938 | Ruskin | 530/407 X |
| 2,492,518 | 12/1949 | Block et al. | 530/358 X |
| 3,681,283 | 8/1972 | Yuett | 530/358 X |
| 4,168,262 | 9/1979 | Kinsella et al. | 530/410 |
| 4,348,479 | 9/1982 | Kinsella et al. | 435/814 X |
| 4,427,580 | 1/1984 | Kinsella et al. | 530/358 |

Primary Examiner—Howard E. Schain
Attorney, Agent, or Firm—Pennie & Edmonds

[57] ABSTRACT

A process for preparing nucleoproteic material which comprises immersing organic material into a suitable solvent for a sufficient time to extract nucleoproteins from said material, adding a sufficient amount of an acid to form a precipitate of nucleoproteic material, and recovering said nucleoproteic material precipitate. A composition of nucleoproteic material produced according to this process. A method for alleviating symptoms of neoplastic diseases which comprises sterilizing the composition of nucleoproteic material, preparing a formulation comprising an effective amount of said sterilized composition, and administering said formulation to a patient having symptoms of a neoplastic disease.

18 Claims, No Drawings

TREATMENT OF SYMPTOMS OF NEOPLASTIC DISEASES WITH NUCLEOPROTEINS

TECHNICAL FIELD

The present invention is related to compositions and methods for the treatment of symptoms of different neoplastic diseases.

BACKGROUND OF THE INVENTION

The histones are body constituents which are presently considered to be of secondary importance in the protection of the body's nucleic acids.

I found that the histones are playing a capital role in biology. The body hierarchic organization is made up of successive entities at various levels. Each basic entity comprises an electropositive principal part bonded to an electropositive secondary part. The principal part remains unchanged, protected by the secondary parts through its adequate changes.

I found the histones to be formed by a series of histosomes, round formations bonded consecutively in a sequence. Each histosome is surrounded by its self-manufactured nucleoproteic material. The histosomes and the nucleoproteic material together form the nucleosomes. The nucleosomes bonded in a row make up the genes. The electropositive histones represent the principal part, with the electronegative nucleoprotein as the secondary part bonded thereto. Together they form the next level in the hierarchy, the genes.

The nucleoproteic material as the active part of the gene is manufactured by the histones as principal part. As the secondary constituent, the nucleoproteic material has the capacity to change. Due to this capacity, nucleoproteic material may be changed through proper external intervention.

Any abnormal body condition corresponds to abnormal nucleoproteic materials, usually with also abnormal histosomes forming together abnormal nucleosomes.

Chronic abnormal conditions, such as neoplastic conditions, can result from the intervention of specific abnormal histones. I have found the histones in general and from the neoplastic material in special to have a specific capacity to possess carcinogenic properties. The histones from the neoplastic material have a specific capacity to possess carcinogenic properties. The repeated injections of these histones into mice have induced the appearance of different tumors at the site of the injections as well as in other parts of the body.

The abnormal conditions which result from the presence of abnormal histones and nucleoproteins give rise to a foreign formation known as isoparasite. The abnormal neoplastic cells are essentially a parasite on the host tissue.

Because of the nucleoproteic material's ability to change, it may be changed by injecting the proper substance. The administration of foreign nucleoproteic material may act as antiabnormal nucleic material and indirectly as antiabnormal histones. The presence of an abnormal entity in a body with its own foreign nucleoproteic material enables this nucleoproteic material to be changed when a new nucleoproteic material is introduced into the body. This has led to the use of such foreign nucleoproteic materials in order to the change the abnormal nucleoproteic material present in lesions.

SUMMARY OF THE INVENTION

The invention relates to a process for preparing nucleoproteic material which comprises immersing organic materials into a suitable solvent for a sufficient time to extract the nucleoproteins from these materials, adding a sufficient amount of an acid to form a precipitate of nucleoproteic material, and recovering said nucleoproteic material precipitate. This precipitate may be washed with distilled water and separated again by centrifugation or filtration.

In this process, a preferred solvent system is water which is slightly alkaline. The material used as a source of nucleoproteins is an organic material, especially full animals or their organs, including at least liver, spleen, intestines, thymus or testes. Microbes, fungi or plants may also be used to obtain nucleoproteins.

Also, the solvent may further comprise an alkaline component, such that the solvent system has a pH between about 7 and 8. The solvent can be heated to boiling to increase the extraction of the desired material. A preferred acid for precipitating nucleoproteins is acetic acid. The resulting precipitate can be recovered by filtration or centrifugation.

Another aspect of the invention relates to compositions of nucleoproteic material produced according to the above-described process.

Preferably, an effective formulation comprises water or alkaline containing about 5-50% of the nucleoproteic composition in suspension. The pH of the formulation may be adjusted with the addition of an alkaline material to a pH range of preferably between 5.5 and 6.5.

The invention also contemplates a method for alleviating symptoms of neoplastic diseases which comprises preparing a formulation comprising an effective amount of the nucleoprotein precipitate, sterilizing this formulation, and administering the formulation to a patient having symptoms of a neoplastic disease. The symptoms of the neoplastic diseases to be alleviated include at least one of pain, anemia, weakness, loss of appetite, nausea and the presence of characteristic abnormal cells and lesions. These formulations are preferably administered by intramuscular injections.

DETAILED DESCRIPTION OF THE PREFERRED EMBODIMENTS

Foreign nucleoproteic material is obtained from a chosen material through extraction by cold, or preferably, by boiling water. The water should preferably be slightly alkaline. This water solution may be then acidified by adding acetic acid or other acids. A precipitate results, which is then separated by centrifugation or filtration. If necessary, this precipitate is treated with sodium hydroxide (NaOH) or another alkaline agent to reach a desired pH of between approximately 5.0 and 6.5. An adequate portion of the product is suspended in water, saline, or other injectable media. The so obtained product is then sterilized for injections. This material is equivalent to nucleoproteins or nucleoproteins which partially may be in the form of salts or esters. Nucleoproteins of any biological material may thus be obtained, each product having a specific capacity to effectively act on a specific pathogenic condition.

An observation of the in vitro (experimentally induced biological processes outside the organism) action upon the cultures of cells, especially the neoplastic cells, will lead to a determination of the most active agents. An observation of in vivo (experimentally induced biological processes in the organism) action upon specific abnormal conditions, especially neoplastic conditions or diseases, is the last means of determining the effectiveness of specific agents upon specific pathological conditions. Neoplastic diseases is used to mean cancers, sarcomas, leukemias, etc.

The nucleoprotein compounds obtained from the entire body or from organs such as the thymus, intestines, liver, spleen and testes of various animals have revealed interesting results against various symptoms. In an attempt to use more specific agents, nucleoprotein compounds obtained from the organs directly involved in the pathological condition are employed. The same may be said for the neutralizing agent if used in obtaining the respective salts or esters of these materials.

A preferred material, carp, is used to provide the nucleoproteins because it is known for its longevity, thus indicating a special ability to resist disease. The thymus, spleen and intestines, in particular, have this special defense capacity. Nucleoproteins obtained from the thymus, spleen, or intestines of carp have resulted in effective action upon different conditions. In general, suspensions from 5% to 50%, preferably approximately 35%, in water or saline are used. This concentration has been determined through experimental and clinical applications in a large variety of acute and chronic abnormal conditions. These conditions include pain, anemia, weakness, loss of appetite and lesions of a neoplastic nature. Good objective and subjective results were obtained in treating neoplastic diseases, such as cancers, sarcomas and leukemia, even after a short treatment by the use of preparations from carp intestines. Pig organs, such as the intestines, are another preferred source of such nucleoproteins.

Especially interesting is the use of the nucleoproteins obtained from microbes, fungi or plants in the treatment of neoplastic conditions in accordance with this invention.

An entire series of pathological conditions has responded within a short time of the administration of different preparations of the invention.

In all cases of cancer treated with these preparations, effects on the existing lesions were objectively and subjectively very favorable. In most of the cases, there was a decrease in pain and the other associated symptoms following the injections. In a few cases, favorable local effects were obtained with only one injection. The changes in the lesions that took place within a short time are indicative of the effective action of these agents upon the lesions themselves.

Alternatively, the precipitated nucleoproteins themselves may be used, instead of their salts or esters. Another alternative that may be utilized is the product obtained by the water extraction, as the material directly extracted through boiling.

The fact that almost all of the subjective and objective results obtained in the different cases of cancer treated were favorable indicates the value of this specific approach in the fight against this disease.

The basic concept of the pathogenic role of specific histones and nucleic material, with the consequent therapeutic use of specific nucleoprotein compounds, is opening an entirely new field in the treatment of general abnormal conditions and specifically in the treatment of various neoplastic conditions.

EXAMPLES

The scope of the invention is further described in connection with the following examples which are set forth for the sole purpose of illustrating the preferred embodiments of the invention and which are not to be construed as limiting the scope of the invention in any manner. In these examples, all parts given are by weight unless otherwise specified.

EXAMPLE 1

W. M., 27 years old, had lymphatic leukemia for years. At the start of the treatment, the blood count showed 186,000 leukocytes. The patient was treated with injections of 3 cc daily of a preparation of 20% of the nucleoproteins of pig intestines. Blood analyses taken every 10 days from the start of the injection showed the following changes in leukocytes: 130,000, 40,000, 12,000, 10,000, and 3,500 leukocytes per cmm. The general condition of the patient progressively became better.

EXAMPLE 2

R. E., 34 years old, had cancer of the stomach, and felt severe pain after eating. The patient was very weak and practically unable to walk. After a week of treatment with 2 daily injections of 2 cc of a preparation of 20% pig intestine nucleoproteins, the patient has been able to walk 9 blocks and eat meat totally without pain.

EXAMPLE 3

Mrs. E. S., 78 years old, had cancer of the breast with a metastases of 5/5 cm on the right clavicule. After 10 days of treatment with a preparation of 1 cc of 20% of the nucleoproteins of pig intestines twice daily, the lesion could no longer be located.

EXAMPLE 4

J. R., 53 years old, with jaundice, cohexia and pain from massive liver metastases, has had pain relieved and strength improved after the injection of 3 cc of a suspension of 20% of pig intestine nucleoproteins, twice daily for one week.

EXAMPLE 5

L. W., 53 years old with very painful left side rib metastases, has had the pain totally controlled after 2 injections of 3 cc of a preparation of a mixture of equal amounts of the nucleoproteins from pig intestines and carp, the mixture totalling a suspension of 20%.

EXAMPLE 6

W. P., had cancer of the esophagus and manifest difficulties in eating. With a teatment of 2 cc daily of a 30% suspension of pig intestines nucleoproteins for one week, all the symptoms have disappeared, and the patient resumed eating normally.

The disappearance of pain, with a general well being sensation was observed in many additional patients, each having different neoplastic conditions, following in general by only a few injections of different nucleoprotein preparations in accordance with the invention and the preceding examples.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A process for preparing pharmaceutical preparations of nucleoproteic material for administration to a subject for treatment of symptoms of neoplastic diseases which comprises:

immersing a carp or pig organ into a solvent for a sufficient time to extract nucleoproteins from said organ;

adding a sufficient amount of an acid to form a precipitate of nucleoproteic material;

sterilizing said nucleoproteic precipitate; and preparing a formulation comprising a sterile water or saline suspension containing about 5 to 50% of said sterilized nucleoproteic precipitate.

2. The process of claim 1 wherein said solvent is water.

3. The process of claim 1 wherein said water is heated to boiling.

4. The process of claim 1 wherein said solvent further comprises an alkaline component.

5. The process of claim 1 wherein said solvent has a pH between about 7 and 8.

6. The process of claim 1 wherein said carp or pig organ is liver, spleen, intestines, thymus or testes.

7. The process of claim 1 wherein said acid is acetic acid.

8. The process of claim 1 wherein said precipitate is recovered by filtration or centrifugation.

9. A process for preparing pharmaceutical preparations of nucleoproteic material for administration to a subject for treatment of symptoms of neoplastic diseases which comprises:

immersing carp thymus, spleen or intestines; pig intestines; or mixtures thereof into water having a pH between about 7 and 8 for a sufficient time to form a solution of nucleoproteins;

adding a sufficient amount of an acid to form a precipitate of nucleoproteic material in suspension in said solution;

filtering or centrifuging said suspension to recover said nucleoproteic material precipitate;

washing the precipitate with distilled water;

reseparating the precipitate by centrifugation or filtration;

sterilizing said nucleoproteic precipitate; and preparing a formulation comprising a sterile water or saline suspension containing about 5 to 50% of said sterilized nucleoproteic precipitate.

10. A pharmaceutical composition of nucleoproteic material produced according to the process of claim 1.

11. A pharmaceutical composition of nucleoprotein material produced according to the process of claim 9.

12. A process for preparing pharmaceutical preparations of nucleoproteic materials for administration to a subject for treatment of symptoms of neuroplastic diseases which comprises:

immersing carp thymus, pig intestines or mixtures thereof into an alkaline solution having a pH of between 7 and 8 for a sufficient time to extract nucleoproteins and form a solution thereof;

adding a sufficient amount of acetic acid to form a precipitate of nucleoproteic material in suspension in said solution;

filtering or centrifuging said suspension to recover said nucleoproteic material precipitate;

washing the precipitate with distilled water;

reseparating the precipitate by centrifugation of filtration;

treating the precipitate with an alkaline agent to obtain a pH therefor of between about 5 and 6.5;

sterilizing said nucleoproteic precipitate; and preparing a formulation comprising a sterile water or on saline suspension containing about 5 to 50% of said sterilized on nucleoproteic precipitate.

13. The process of claim 12 wherein the suspension comprises between 20 and 35% of the nucleoproteic precipitate.

14. The process of claim 9 wherein the suspension comprises between 20 and 35% of the nucleoproteic precipitate.

15. The process of claim 1 wherein the suspension comprises between 20 and 35% of the nucleoproteic precipitate.

16. The process of claim 12 wherein the water is heated to boiling to facilitate the extraction of said nucleoproteins.

17. The process of claim 9 wherein the water is heated to boiling to facilitate the extraction of said nucleoproteins.

18. A pharmaceutical composition of nucleoproteic material produced according to the process of claim 12.

* * * * *